(12) United States Patent
Young et al.

(10) Patent No.: US 10,620,175 B2
(45) Date of Patent: Apr. 14, 2020

(54) APPARATUS AND PROCESSES FOR PHOTOSYNTHETIC ACTIVITY MEASUREMENT AND MAPPING

(71) Applicant: RAYTHEON COMPANY, Waltham, MA (US)

(72) Inventors: Darrell L. Young, Falls Church, VA (US); Charlotte DeKeyrel, Leesburg, VA (US); Michael Henry Lewis, Leesburg, VA (US)

(73) Assignee: RAYTHEON COMPANY, Waltham, MA (US)

( * ) Notice: Subject to any disclaimer, the term of this patent is extended or adjusted under 35 U.S.C. 154(b) by 554 days.

(21) Appl. No.: 15/153,789

(22) Filed: May 13, 2016

(65) Prior Publication Data

US 2016/0335477 A1   Nov. 17, 2016

Related U.S. Application Data

(60) Provisional application No. 62/160,881, filed on May 13, 2015.

(51) Int. Cl.
| | | |
|---|---|---|
| G01N 33/00 | (2006.01) | |
| G01N 21/59 | (2006.01) | |
| G01N 21/47 | (2006.01) | |
| G06K 9/00 | (2006.01) | |
| G06K 9/46 | (2006.01) | |
| G01N 21/31 | (2006.01) | |
| G01N 21/3563 | (2014.01) | |
| G01N 21/359 | (2014.01) | |
| G01N 21/84 | (2006.01) | |

(52) U.S. Cl.
CPC ......... *G01N 33/0098* (2013.01); *G01N 21/31* (2013.01); *G01N 21/4738* (2013.01);
(Continued)

(58) Field of Classification Search
CPC ............... G01N 33/0098; G01N 21/31; G01N 21/3563; G01N 21/359; G01N 21/4738;
(Continued)

(56) References Cited

U.S. PATENT DOCUMENTS

| | | | |
|---|---|---|---|
| 8,391,565 B2 | 3/2013 | Purcell et al. | |
| 2005/0072935 A1* | 4/2005 | Lussier | G01N 21/6456 |
| | | | 250/458.1 |

(Continued)

FOREIGN PATENT DOCUMENTS

CN          108663330 A     * 10/2018

OTHER PUBLICATIONS

Patane et al., "Chlorophyll and Nitrogen Estimation Techniques: A Review", International Journal of Engineering Research and Reviews, vol. 2, Issue 4, 2014, pp. 33-41.

(Continued)

*Primary Examiner* — Pinalben Patel
(74) *Attorney, Agent, or Firm* — Lando & Anastasi, LLP

(57) ABSTRACT

A method for determining chlorophyll content of a plant comprises capturing a first image comprising light transmitted through a leaf of a plant; capturing a second image comprising light reflected from the leaf of the plant; estimating, from a plurality of pixels in the first image, a transmissive chlorophyll concentration value of the leaf; estimating a reflectance chlorophyll concentration value for the leaf from a plurality of pixels in the second image using bidirectional reflectance parameters for which a variance of the reflectance chlorophyll concentration value across the plurality of pixels in the second image is reduced; and determining an estimated chlorophyll concentration value for the plant based at least on the transmissive chlorophyll concentration value and the reflectance chlorophyll concentration value.

20 Claims, 7 Drawing Sheets

(52) U.S. Cl.
CPC ......... *G01N 21/59* (2013.01); *G06K 9/00147* (2013.01); *G06K 9/4661* (2013.01); *G01N 21/359* (2013.01); *G01N 21/3563* (2013.01); *G01N 2021/8466* (2013.01)

(58) Field of Classification Search
CPC ........... G01N 21/59; G01N 2021/8466; G06K 9/00147; G06K 9/4661
See application file for complete search history.

(56) References Cited

U.S. PATENT DOCUMENTS

| | | | |
|---|---|---|---|
| 2011/0047636 A1* | 2/2011 | Stachon | A01G 7/00 800/260 |
| 2011/0135161 A1* | 6/2011 | Koutsky | A01H 1/04 382/110 |
| 2013/0044919 A1* | 2/2013 | Purcell | G01N 21/25 382/110 |
| 2015/0015697 A1* | 1/2015 | Redden | G01N 33/0098 348/89 |
| 2015/0359183 A1* | 12/2015 | Green | A01N 25/00 504/292 |
| 2016/0216245 A1* | 7/2016 | Sutton | G01N 33/0098 |
| 2018/0003686 A1* | 1/2018 | Ozcan | G01N 21/274 |

OTHER PUBLICATIONS

Jacquemoud et al., "PROSPECT: A Model of Leaf Optical Properties Spectra" Remote Sens. Environ., vol. 34, 1990, pp. 75-91.

Jiang et al., "What is the Space of Spectral Sensitivity Functions for Digital Color Cameras?", IEEE, Conference: Applications of Computer Vision (WACV), 2013, pp. 4321-4328. DOI: 10.1109/WACV.2013.6475015.

* cited by examiner

APPARATUS AND PROCESSES FOR PHOTOSYNTHETIC ACTIVITY MEASUREMENT AND MAPPING

RELATED APPLICATIONS

This application claims priority under 35 U.S.C. § 119(e) to U.S. Provisional App. No. 62/160,881, entitled "APPARATUS AND PROCESSES FOR A PHOTOSYNTHETIC ACTIVITY MAPPING APPLICATION," filed May 13, 2015, which application is incorporated herein by reference in its entirety.

BACKGROUND

Nitrogen fertilizer is one of the main costs associated with growing food crops, including grain crops such as corn, wheat, and rice. To a point, nitrogen increases crop yield at a very cost-efficient rate; beyond that point, some amount of over-application does not harm the plant. Farmers therefore often err on the side of caution by over-applying nitrogen fertilizer to their crops. World-wide annual consumption of nitrogen fertilizer is 500 million short tons, up to an estimated 50% of which is not needed to achieve optimum yield.

There are downsides to the over-application of nitrogen fertilizer, including the needless expense to the grower and the risks posed to water and other aspects of the ecosystem affected by runoff. It would therefore be advantageous to accurately identify an optimal amount of nitrogen fertilizer to be applied to maximize yield of the crop without using more than needed.

Nitrogen content and chlorophyll content in a plant are interrelated, so by estimating the amount of chlorophyll in a plant, the amount of nitrogen present (and therefore the amount of nitrogen to be applied) can be determined. Known techniques for estimating chlorophyll from images of the plant rely on the color of the leaf. Yet "color" describes the response of the eyes and brain to the visible spectrum, and is therefore inapplicable and unreliable in computer-based chlorophyll measurement. Estimating chlorophyll content also requires information about the structure of the leaf, including its index of refraction, which varies from species to species. Known methods typically used a "published" value of a leaf model parameter, N. Yet this approximation of N for a given leaf does not take into account the actual variations in N from leaf to leaf.

SUMMARY OF THE INVENTION

Aspects and embodiments are directed to apparatus and methods for processing digital images of plant leaves to estimate a level of chlorophyll in the plant. Images of light transmitted through, and reflected from, the leaf is used. The issue of bidirectional reflectance is addressed by assigning initial bidirectional reference parameters to the pixels of the image of reflected light and estimating a chlorophyll level for each pixel using those parameters. The bidirectional reference parameters are iterated according to the estimated chlorophyll level, and the process repeats until a chlorophyll level of the leaf is converged upon for which there is minimal variance across the pixels. The difference between the chlorophyll estimates obtained using the transmitted and reflected light is used to re-estimate a model parameter relating to an index of refraction of the leaf, and new estimates are generated using the revised model parameter.

One or more spot chlorophyll measurements taken in such a manner can be used to correct and calibrate overhead imagery of the crop, allowing for the creation of an overhead chlorophyll model refined by the spot measurements. The chlorophyll model is used to generate a nitrogen sufficiency map, which in turn allows for the creation of recommendations for the application of nitrogen at locations in the field where the nitrogen level is insufficient. Spot yield measurements and historical data can be used to further refine the overhead model and nitrogen recommendations.

According to one aspect, a method for determining chlorophyll content of a plant includes capturing a first image comprising light transmitted through a leaf of a plant; capturing a second image comprising light reflected from the leaf of the plant; estimating, from a plurality of pixels in the first image, a transmissive chlorophyll concentration value of the leaf; estimating a reflectance chlorophyll concentration value for the leaf from a plurality of pixels in the second image using bidirectional reflectance parameters for which a variance of the reflectance chlorophyll concentration value across the plurality of pixels in the second image is reduced; and determining an estimated chlorophyll concentration value for the plant based at least on the transmissive chlorophyll concentration value and the reflectance chlorophyll concentration value.

According to one embodiment, the transmissive chlorophyll concentration value and the reflectance chlorophyll concentration value are determined using a leaf model parameter, and the method further includes estimating, from the transmissive chlorophyll concentration value and the reflectance chlorophyll concentration value, a revised leaf model parameter; and determining a second transmissive chlorophyll concentration value and a second reflectance chlorophyll concentration value using the revised leaf model parameter. According to a further embodiment, the revised leaf model parameter is estimated based on a difference between the transmissive chlorophyll concentration value and the reflectance chlorophyll concentration value. According to yet another embodiment, estimating, from the plurality of pixels in the first image, the transmissive chlorophyll concentration value of the leaf includes determining, from sensor spectral response characteristics of each pixel in the plurality of pixels in the first image, a triangular greenness index (TGI) for the pixel.

According to one embodiment, the method further includes capturing a third image comprising light passed through a first medium and a fourth image comprising light passed through a second medium, the first medium and second medium having transmissive characteristics corresponding to known transmissive chlorophyll levels; and adjusting the transmissive chlorophyll concentration value of the leaf with reference to the known transmissive chlorophyll levels. According to a further embodiment, the first medium has transmissive characteristics corresponding to a known low transmissive chlorophyll level, and the second medium has transmissive characteristics corresponding to a known high transmissive chlorophyll level.

According to another embodiment, the method further includes estimating, using a bidirectional reflectance parameter for each pixel in the plurality of pixels, a first reflectance chlorophyll concentration pixel value for each pixel in the plurality of pixels; determining a first variance of the first reflectance chlorophyll concentration pixel value across the plurality of pixels; modifying the bidirectional reflectance parameter for at least one pixel in the plurality of pixels; estimating, using the modified bidirectional reflectance parameter for the at least one pixel, a second reflectance chlorophyll concentration pixel value for each pixel in the plurality of pixels; determining a second variance of the second reflectance chlorophyll concentration pixel value across the plurality of pixels; responsive to the first variance being less than the second variance, estimating the reflectance chlorophyll concentration value based on the first reflectance chlorophyll concentration pixel value of the leaf for each pixel in the plurality of pixels; and responsive to the second variance being less than the first variance, estimating the reflectance chlorophyll concentration value based on the second reflectance chlorophyll concentration pixel value of the leaf for each pixel in the plurality of pixels.

According to a further embodiment, modifying the bidirectional reflectance parameter for at least one pixel in the plurality of pixels includes, responsive to the at least one pixel in the plurality of pixels having a relatively high first reflectance chlorophyll concentration pixel value, adjusting the bidirectional reflectance parameter of the at least one pixel to be lower; and responsive to the at least one pixel in the plurality of pixels having a relatively low first reflectance chlorophyll concentration pixel value, adjusting the bidirectional reflectance parameter of the at least one pixel to be higher. According to a further embodiment, estimating the reflectance chlorophyll concentration value based on the second reflectance chlorophyll concentration pixel value of the leaf for each pixel in the plurality of pixels includes determining a mean of the second reflectance chlorophyll concentration pixel value of the leaf for the plurality of pixels.

According to a further embodiment, the method further includes excluding, from the determination of the mean, pixels having a modified bidirectional reflectance parameter not within a defined deviation amount.

According to a still further embodiment, the bidirectional reflectance parameter is an initial bidirectional reflectance parameter, and the method further includes setting an initial bidirectional reflectance parameter for at least one pixel in the plurality of pixels, the initial bidirectional reflectance parameter determined by the sensor spectral response measurement of the at least one pixel.

According to a still further embodiment, the method further includes setting a first initial bidirectional reflectance parameter of 0.6 for at least one pixel having a highest sensor spectral response measurement in the plurality of pixels, and setting a second initial bidirectional reflectance parameter of 0.0 for at least one pixel having a lowest sensor spectral response measurement in the plurality of pixels.

According to one embodiment, the plant is a first plant, and the method further includes estimating a second transmissive chlorophyll concentration value and a second reflectance chlorophyll concentration value for at least a second plant in a crop field including the first plant; and generating a model of plant health for the crop field based at least on the transmissive chlorophyll concentration value, the reflectance chlorophyll concentration value, the second transmissive chlorophyll concentration value and the second reflectance chlorophyll concentration value. According to a further embodiment, the model of plant health for the crop field is a chlorophyll model indicating an estimated chlorophyll level of plants in a plurality of locations in the crop field.

According to another embodiment, the plant is a corn plant.

According to another aspect, an image processing system includes a memory; an image receiving component; and a processor configured to capture a first image comprising light transmitted through a leaf of a plant; capture a second image comprising light reflected from the leaf of the plant; estimate, from a plurality of pixels in the first image, a transmissive chlorophyll concentration value of the leaf; estimate a reflectance chlorophyll concentration value for the leaf from a plurality of pixels in the second image using bidirectional reflectance parameters for which a variance of the reflectance chlorophyll concentration value across the plurality of pixels in the second image is reduced; and determine an estimated chlorophyll concentration value for the plant based at least on the transmissive chlorophyll concentration value and the reflectance chlorophyll concentration value.

According to one embodiment, the image receiving component is a digital camera of a mobile device. According to another embodiment, the image processing system further includes an optical reference having a first medium and a second medium, the first medium and second medium having transmissive characteristics corresponding to known transmissive chlorophyll levels, and the processor is further configured to capture a third image comprising light passed through the first medium and a fourth image comprising light passed through the second medium; and adjust the transmissive chlorophyll concentration value of the leaf with reference to the known transmissive chlorophyll levels.

According to another embodiment, the processor is further configured to estimate, using a bidirectional reflectance parameter for each pixel in the plurality of pixels, a first reflectance chlorophyll concentration pixel value for each pixel in the plurality of pixels; determine a first variance of the first reflectance chlorophyll concentration pixel value across the plurality of pixels; modify the bidirectional reflectance parameter for at least one pixel in the plurality of pixels; estimate, using the modified bidirectional reflectance parameter for the at least one pixel, a second reflectance chlorophyll concentration pixel value for each pixel in the plurality of pixels; determine a second variance of the second reflectance chlorophyll concentration pixel value across the plurality of pixels; responsive to the first variance being less than the second variance, estimate the reflectance chlorophyll concentration value based on the first reflectance chlorophyll concentration pixel value of the leaf for each pixel in the plurality of pixels; and responsive to the second variance being less than the first variance, estimate the reflectance chlorophyll concentration value based on the second reflectance chlorophyll concentration pixel value of the leaf for each pixel in the plurality of pixels.

According to a further embodiment, the processor is further configured to modify the bidirectional reflectance parameter for at least one pixel in the plurality of pixels by, responsive to the at least one pixel in the plurality of pixels having a relatively high first reflectance chlorophyll concentration pixel value, adjusting the bidirectional reflectance parameter of the at least one pixel to be lower; and responsive to the at least one pixel in the plurality of pixels having a relatively low first reflectance chlorophyll concentration pixel value, adjusting the bidirectional reflectance parameter of the at least one pixel to be higher.

According to another aspect, a method of determining a nitrogen content of a field crop includes determining, from an image of an individual plant leaf from a first plant in a field, an estimate of a chlorophyll concentration value of the first plant in a first region in the field; detecting, in an overhead image of the field, an overhead sensor spectral response measurement of at least one second plant in the first region in the field; and generating, based on the estimate of the chlorophyll concentration value of the individual plant leaf and the overhead sensor spectral response measurement of the at least one second plant, a map of estimated chlorophyll concentrations of plants in a portion of the field.

According to a further embodiment, the overhead sensor spectral response measurement of the at least one second plant is a triangular green index (TGI). According to a further embodiment, the method further includes determining, from a ground-based image of at least one third plant and surrounding soil in the first region, a ground-based sensor spectral response measurement of the at least one third plant; and adjusting the overhead sensor spectral response measurement of the at least one second plant based on the ground-based sensor spectral response measurement.

According to a further embodiment, the method includes identifying at least one dimension of a row of plants in which the at least one third plant is located. According to a further embodiment, the method includes generating, based on the map of estimated chlorophyll concentrations of plants in a portion of the field, at least one recommendation for applying nitrogen to the first region of the field.

According to a further embodiment, the method includes determining, from an image of a grain seed head of a third plant in the first region of the field, an estimated yield of the third plant; and modifying the at least one recommendation for applying nitrogen to the first region of the field based on the estimated yield of the third plant.

Still other aspects, embodiments, and advantages of these exemplary aspects and embodiments are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure. In the figures.

DETAILED DESCRIPTION

Figure 1:
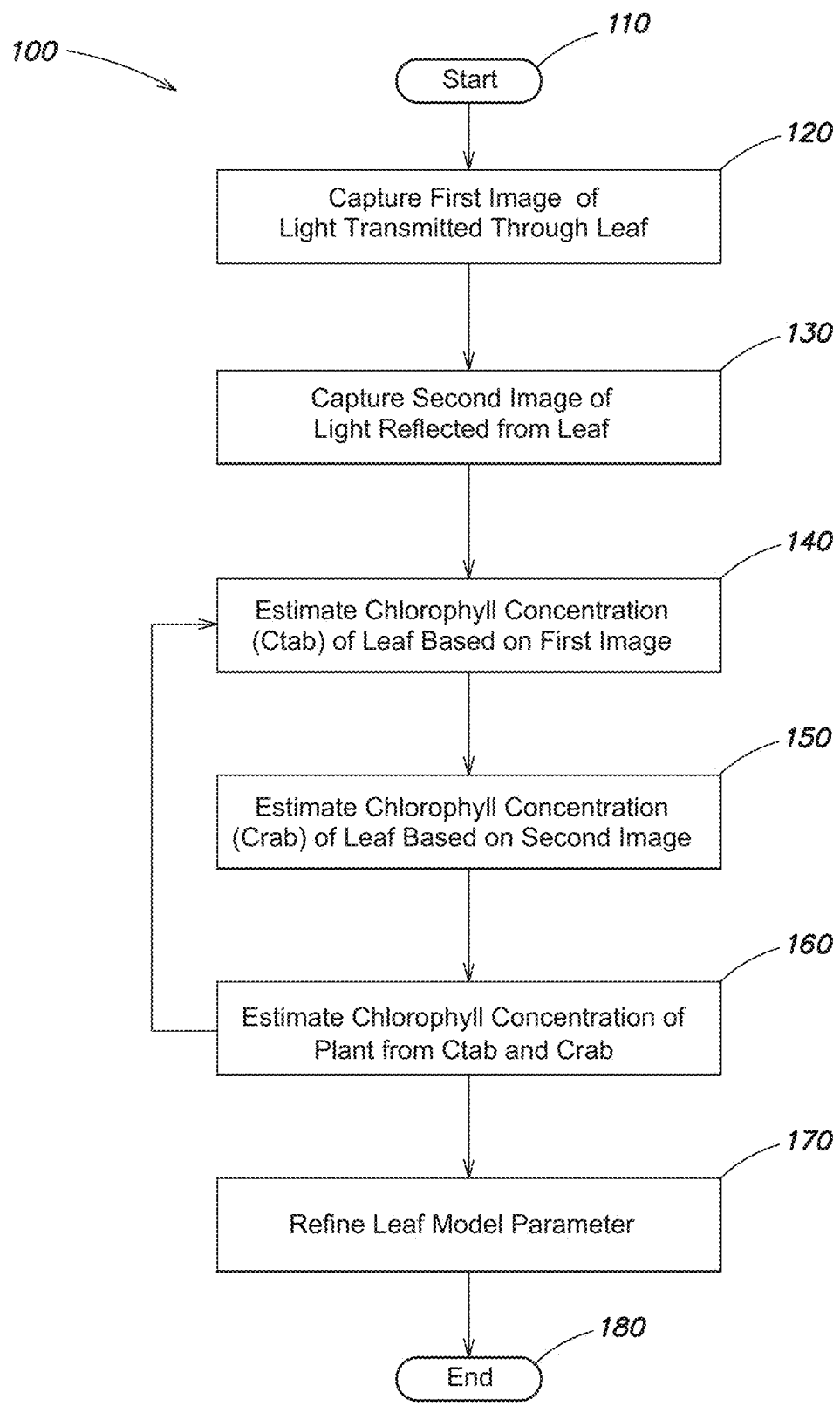
FIG. 1 illustrates an exemplary method of estimating the chlorophyll level of a leaf as discussed in various embodiments herein.

The ability to capture and process images of leaves and other foliage, and used those images to estimate a chlorophyll level of the plant, enables a user to estimate an amount of nitrogen available to the plant, and, if necessary, an amount of nitrogen to be applied via "side dress" fertilizing or other means. Aspects and embodiments are directed to capturing a first image of light transmitted through a leaf, and capturing a second image of light reflected off the leaf. The first image is processed to estimate a chlorophyll a+b level from the transmitted light using coefficients related to N, the parameter that models the leaf's index of refraction.

The second image is processed to estimate a chlorophyll a+b level from the reflected light using coefficients related to N. To reduce the effect of glint/glare, incidence angle, and other complicating factors introduced in when reflected light is photographed, each pixel of the image is assigned an initial bidirectional reflectance parameter (Bspec). A chlorophyll a+b level is estimated from the reflected light using the initial Bspec value for each pixel. The initial Bspec values are then adjusted based on the estimated chlorophyll level for each pixel, on the assumption that the chlorophyll level will be relatively consistent throughout the leaf. The adjustment of Bspec values continues in an iterative manner until a combination of Bspec values is found for the pixels that yields minimal variance of estimated chlorophyll across the pixels. By converging on the estimated chlorophyll level in this manner, the effect of Bpsec sensitivity in determining estimated chlorophyll is reduced.

Once estimates of the chlorophyll levels have been determined from the transmitted light and the reflected light, the two measurements can be compared, and their relationship can be used to re-estimate the model parameter N. The chlorophyll levels can then be re-estimated using the revised value of N, allowing for a more accurate chlorophyll estimate.

A number of spot measurements of chlorophyll taken in this manner can be used to generate a full chlorophyll model of the field, which in turn can be used to generate nitrogen sufficiency maps.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

FIG. 1 is a flow diagram for one example of a method 100 for determining chlorophyll content of a plant.

Method 100 begins at step 110.

At step 120, a first image is captured comprising light transmitted through a leaf of a plant grown in a crop field, and at step 130, a second image is captured comprising light reflected from the leaf of the plant. The first image and the second image may be captured by a digital camera, or by a mobile device (e.g., a cell phone or tablet) with a camera and image-capturing capabilities. The use of a mobile device may allow the images to be captured in a field of crops (e.g., a corn field) in which the plant is growing. In other embodiments, the image is not directly captured, but may be received over a network, on a disk, or otherwise provided to the system for processing.

To capture the first image of light transmitted through the leaf of the plant grown in the crop field, the leaf is held directly adjacent to and in contact with the lens of the camera. In some embodiments, the plant is a corn plant, and the leaf is a husk of the corn. It will be appreciated, however, that the embodiments disclosed herein can be carried out on leaves of a variety of plants without departing from the spirit of the disclosure. A clamp, fixture, or other component may be utilized to hold the leaf at a distance and orientation relative to the lens suitable for creating the first image. With the leaf in position, the first image is created when light passes through the leaf and strikes the camera sensor on which the image is formed.

Figure 2A:
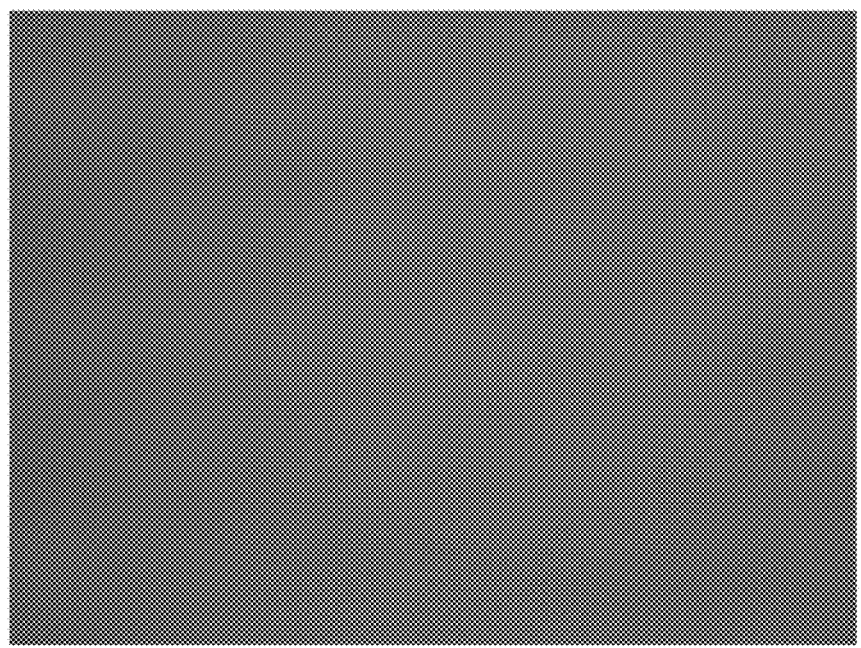
FIG. 2A illustrates an exemplary first image (reproduced in grayscale) of light transmitted through a leaf according to aspects of the invention.
Figure 2B:
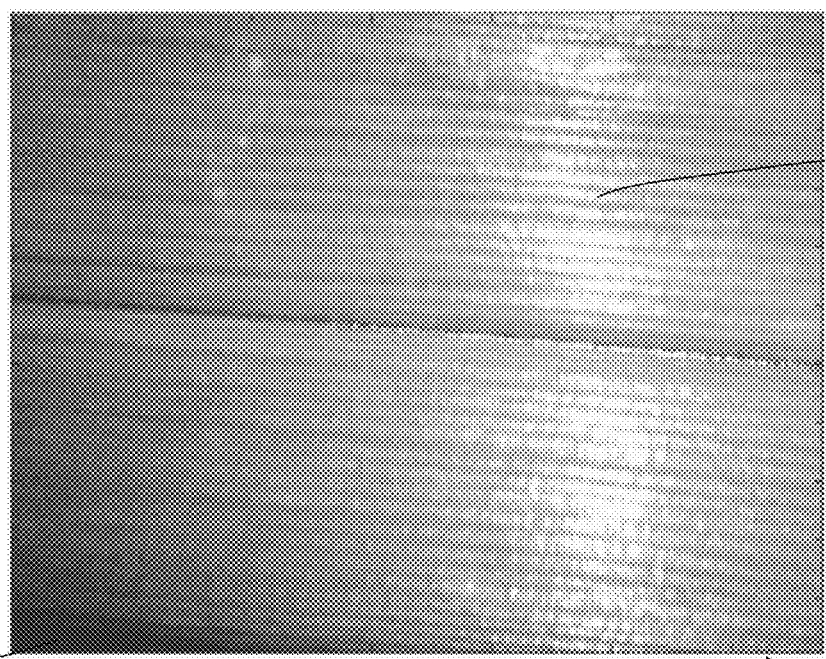
FIG. 2B illustrates an exemplary second image (reproduced in grayscale) of light reflected from a leaf according to aspects of the invention.

Exemplary first image 200A and second image 200B are seen in FIGS. 2A and 2B, respectively. Though the first image 200A and the second image 200B are shown here in grayscale for ease of reproduction, it is to be expected that the first image 200A and the second image 200B will include one or more shades of green color depending on the type of leaf and/or its chlorophyll content.

To capture the second image of light reflected from the leaf of the plant, the leaf may be held at a set distance from the camera lens. A clamp, fixture, or other component may be utilized to hold the leaf at a distance and orientation relative to the lens suitable for creating the second image. With the leaf in position, the second image is created when light reflects off the leaf and strikes the camera sensor on which the image is formed.

An exemplary second image 200B is seen in FIG. 2B. Because the second image 200B is created by reflected light, areas of different brightness are present due to the orientation and characteristics of the leaf, the light source (e.g., the sun), and/or the camera lens used to capture the second image. For example, a "glint" of light reflected from the leaf can be seen in an area of relatively high brightness surrounding pixel 210. A relatively darker area of the leaf, due to the relatively lower amount of light it reflects, can be seen in an area of relatively low brightness surrounding pixel 220.

The first image and the second image may be created using the same leaf, or may be created using different leaves having certain characteristics in common, including color, thickness, location of the plant from which it was harvested, elapsed time since picking, or other characteristics.

Images created by light that is either transmitted through the leaf (as in the first image) or reflected off the leaf (as in the second image) are sensitive to differences in lighting conditions, and images captured in certain lighting conditions may allow the embodiments described herein to be performed with a higher degree of accuracy. In some embodiments, therefore, certain lighting conditions may be enforced or suggested. For example, it may be a requirement that the first image and/or second image are captured during periods of bright sunlight. It may also be a requirement that the second image (of reflected light) be captured when the sun is substantially overhead, or in another known position. Information about weather forecasts, sun position, and other meteorological information may be accessed to aid in predicting or otherwise determining suitable conditions for capturing the first image and/or the second image. In some embodiments, suggestions or instructions for suitable times and/or weather conditions may be provided. For example, the mobile device may display information indicating that suitable conditions are expected between 11:15 am and 1:45 pm on an upcoming day during which to capture the second image. In some embodiments, artificial light sources may be used. Different lighting conditions may be suitable for different devices according to their digital camera sensitivity functions. In some embodiments, sensitivity functions for known device models may be accessed from a database in determining whether lighting conditions are suitable. In other embodiments, the sensitivity function of the device may be estimated or determined using known techniques as part of a pre-process or calibration process.

Additional constraints may be imposed under which the first image and/or the second image will be captured. For example, attempts to capture the second image may be affected by bright areas of light, or glint, reflecting off the surface of the leaf. In some embodiments, the mobile device may provide an indication that undesirable lighting conditions (like excessive glint) are present, and may delay attempts to capture the second image until the lighting conditions are corrected.

Once captured, the size or other characteristics of the first image and/or second image may also be validated or modified as necessary. For example, if the image is of too low a resolution, size, contrast, or sharpness, it may be assumed that the method cannot be performed on the image in a manner yielding sufficiently accurate results. As a result, an attempt to perform the method on an image having an inadequate resolution (e.g., less than 2 megapixels), size, contrast, or sharpness may be aborted by the system, and an error message may be displayed on the mobile device or elsewhere indicating that the image is deficient, as well as information identifying the deficiency.

On the other hand, while digital cameras and devices are currently able to capture relatively high-resolution images, and typically do so by default, it may be determined in some embodiments that such high resolution is not necessary for performance of the method. Furthermore, the large file sizes associated with such high-resolution images may require an unnecessary amount of time and resources to process. The image may therefore be downsampled to a lower resolution that reduces file size while still providing sufficient resolution for the image processing steps described herein. Downsampling the image to a standardized resolution may also simplify subsequent processing steps, as there would be no need to provide for the processing of images having different resolutions. In a preferred embodiment, the image may be downsampled to 2 megapixels. In other embodiments, the resulting resolution may be set by the system or a user, or may be determined at runtime by taking into account such factors as the file size, resolution, or dimensions of the original image, or the currently available processing bandwidth of the system.

The image may also be preliminarily processed to verify the likely existence and position a leaf in the image, as well as the leaf's suitability for use in subsequent steps. In some embodiments, the image is analyzed to locate a region matching the expected characteristics of an image of a leaf, such as a generally green color and a relatively uniform composition.

To further streamline processing, the image may be cropped to the region corresponding to a portion of the leaf on which subsequent steps are likely to yield accurate results. For example, computer vision or other image processing techniques may be performed so as to exclude regions of the image that include stems, veins, damaged regions of the leaf, or other characteristics that may negatively affect processing. The image may also be resized to standardized dimensions to reduce the complexity of later processing steps.

At step 140, a chlorophyll concentration value of the leaf is estimated based on the first image of transmitted light through the leaf. In some embodiments, the RGB values $R_t$, $G_t$, $B_t$ of the pixels of the first image are de-mosaicked to construct a full color image. (The subscript "t" denotes that these RGB values are derived from the first image, comprising light transmitted through the leaf). A chlorophyll concentration of the leaf can be estimated from the $R_t$, $G_t$, $B_t$ values.

A triangular green index (TGI) may be estimated from the $R_t$, $G_t$, $B_t$ values. "A visible band index for remote sensing leaf chlorophyll content at the canopy scale" (2013), by Hunt, E. Raymond Jr., et al., the disclosure of which is hereby incorporated by reference in the entirety. TGI is a spectral index for describing imaging spectrometry data in the visible-band spectrum. In some embodiments, the relationship of TGI to the RGB values of the transmissive image can be expressed as:

$$TGI_t = \tfrac{1}{2}(190(R_t-G_t)-120(R_t-B_t))$$

A transmissive measure of chlorophyll a+b (Ctab) in the leaf from the may be estimated based on the value of TGI and one or more transmissive model coefficients related to a leaf model parameter N. N relates to an index of refraction of the leaf, and may be a known or approximate value that varies by plant type, leaf structure, vascularization, and the like. For example, a monocot plant may have an N of 1.5, whereas a dicot may have an N of 3. In some embodiments, the relationship between Ctab and the coefficients may be expressed as a second order polynomial having three coefficients a, b, and c. In such embodiments, an initial value of N may be estimated based on known characteristics of the plant and/or leaf, and the corresponding transmissive model coefficients a, b, and c may be derived or accessed for that value of N. In some embodiments, a database of approximate N values and corresponding coefficient values is accessed; coefficients for the N selected for use in the current model may be interpolated or otherwise estimated from transmissive model coefficients for known values of N. In other embodiments, the coefficient values may be calculated using N and the $R_t$, $G_t$, $B_t$ values.

An exemplary table of transmissive model coefficients for representative values of N is shown in Table 1:

TABLE 1

Exemplary transmissive coefficients for various values of N

| N | a | B | c |
|---|---|---|---|
| 1 | 0.006546 | 1.7687 | 138.71 |
| 1.5 | 0.011760 | 2.2295 | 127.28 |
| 2 | 0.019220 | 2.7156 | 118.50 |
| 2.5 | 0.029778 | 3.2515 | 111.75 |
| 3 | 0.044475 | 3.8492 | 106.45 |

The value of $TGI_t$ and the coefficients for a given N may be used in calculating the estimated chlorophyll, Ctab, in the leaf, where:

$$Ctab = a(TGI_t^2) + b(TGI_t) + c$$

Figure 3:
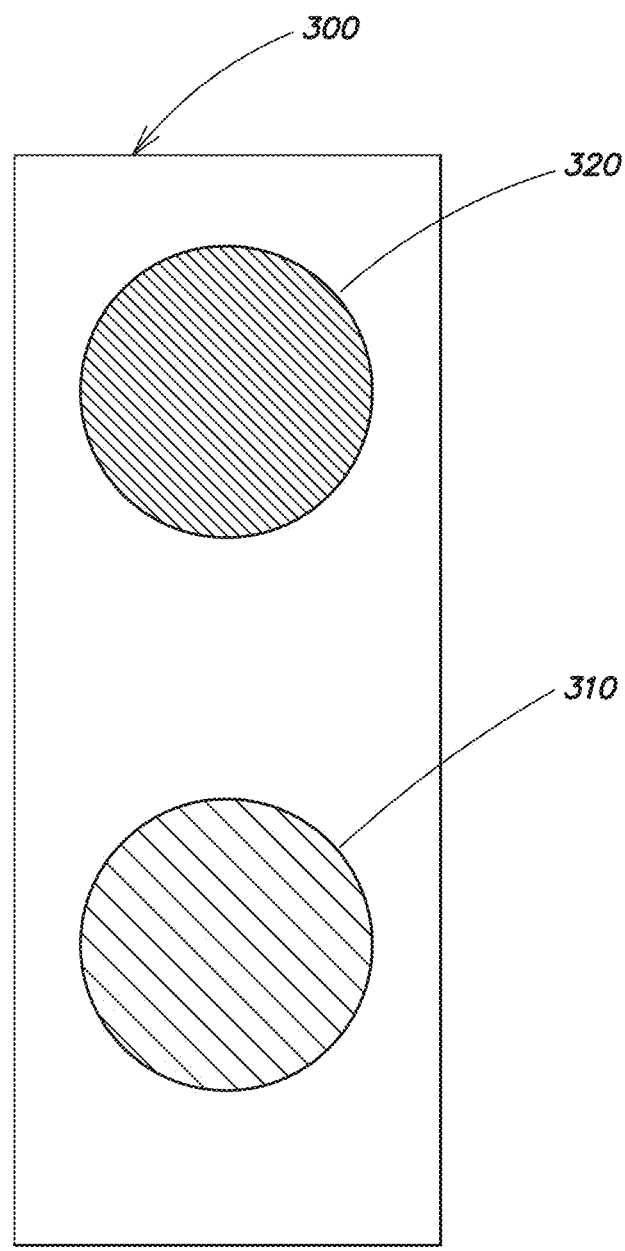
FIG. 3 illustrates an optical reference card for calibrating chlorophyll measurements according to aspects of the invention.

In some embodiments, one or more optical references are used to adjust the value of Ctab by correlating the $R_t$, $G_t$, $B_t$ values in the first image with R, G, B values obtained through media having characteristics associated with known chlorophyll levels. For example, images may be captured through two semi-transparent films on an optical reference card. An exemplary optical reference card 200 is seen in FIG. 3. A first window 310 is provided that allows the transmission of light in a manner that emulates the transmission of light a leaf having a known low chlorophyll level of a plant, and a second window 320 is provided that allows the transmission of light in a manner that emulates the transmission of light a leaf having a known high chlorophyll level of a plant. In some embodiments, only a single window is provided. The first window 310 and the second window 320 may be constructed of plastic, vellum, paper, or other transparent or semi-transparent material, and may be tinted or otherwise made to emulate the light-transmissive characteristics of a leaf.

In embodiments where the optical reference card 300 is used, a correction factor B to be used in calculating Ctab may be determined by the RGB values of the images captured through the first window 310 and the second window 320. For example, a linear error equation may be interpolated between the RGB values of the images captured through the first window 310 and the second window 320 using the value of Ctab determined above. The interpolation yields the correction factor B for a known value of N, which can be used to calculate a refined value of Ctab:

$$Ctab = a(TGI_t^2) + b(TGI_t) + c + B$$

The correction factor B may allow for the correction of errors or inaccuracies in calculating the Ctab due to lighting conditions in capturing the first image.

Returning again to FIG. 1, at step 150 a reflectance chlorophyll concentration value is estimated for the leaf based on the second image of light reflected off the leaf. In some embodiments, the RGB values $R_r$, $G_r$, $B_r$ of the pixels of the second image are de-mosaicked to construct a full color image. (The subscript "r" denotes that these RGB values are derived from the second image, comprising light reflected from the leaf). A chlorophyll concentration of the leaf can be estimated using the $R_r$, $G_r$, $B_r$ values.

Measuring reflected light introduces the complication of bidirectional reflectance, which includes such factors as the illumination zenith angle $\theta_s$, the incident angle $\theta_i$, and the bidirectional reflectance distribution function (BRDF) parameter, Bspec. A Bspec value may be determined for each pixel in an image, and may vary greatly due to certain reflectance phenomena. For example, Bspec for pixels in an image of a leaf may have a maximum value of 0.6 in the center of a glint, and may have a minimum value of 0 where the image is captured at high incidence angles, or where regions of the leaf are damaged. In other embodiments, a different minimum value (e.g., 0.2) may be set for Bpsec for pixels.

A reflectance measure of chlorophyll a+b (Crab) in the leaf from the may be estimated based in part on the value of Bspec. Yet embodiments of the present disclosure avoid the inaccuracies associated with the wide variance in Bspec values described above by simultaneously estimating Bspec and Crab under the constraint of minimizing Crab variance across the leaf surface. The level of chlorophyll across a relatively uniform, undamaged leaf may be presumed to be consistent. Determining Crab using iterating estimated values of Bspec for each pixel of the second image, with the goal of minimizing variance in the Crab, therefore allows the method to converge on an accurate estimate of Crab.

Figure 4:
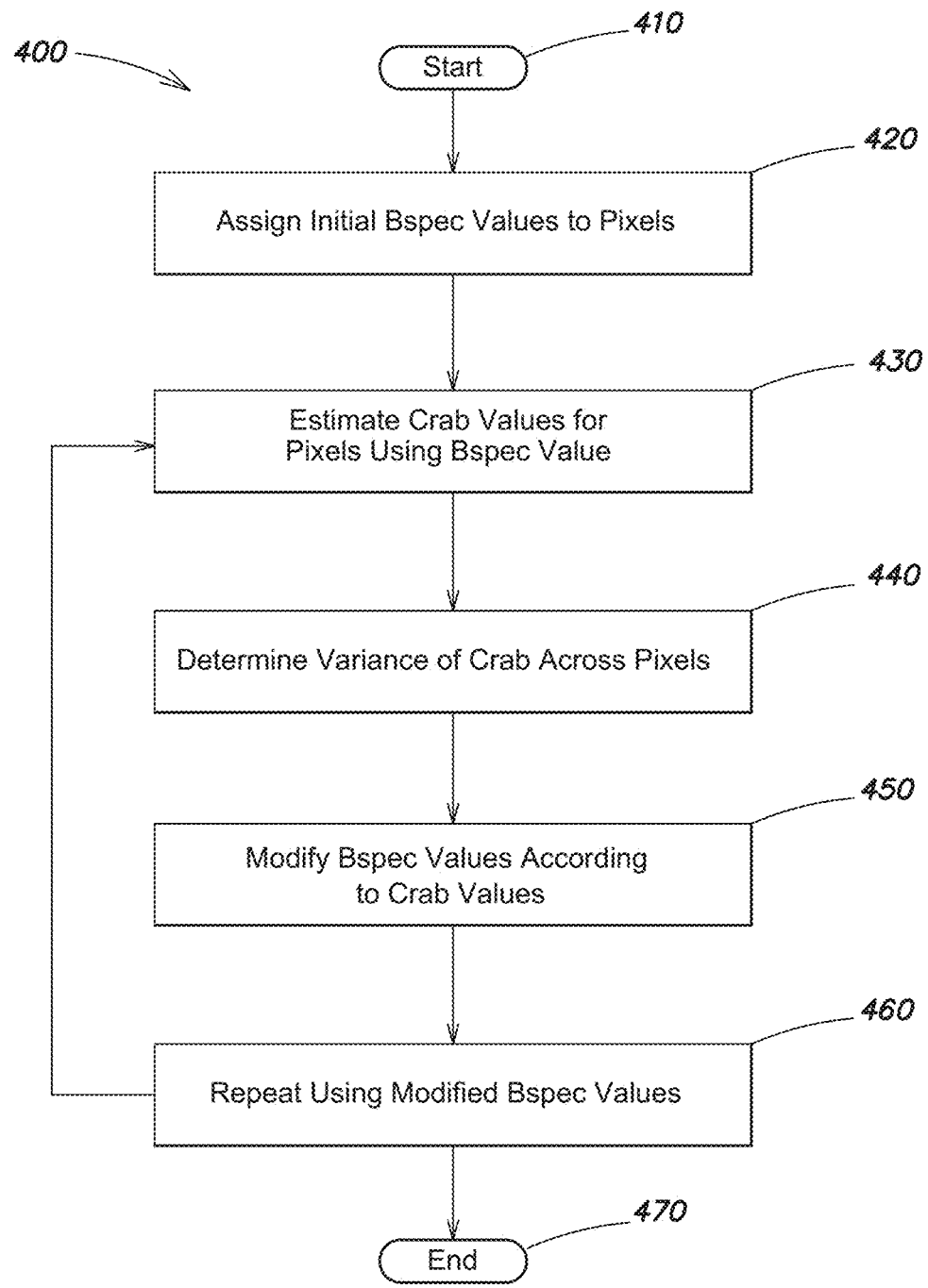
FIG. 4 illustrates an exemplary method of estimating a chlorophyll level from the leaf of the second image of FIG. 2B as discussed in various embodiments herein.

A method 400 of converging on an accurate estimate of Crab according to one embodiment is discussed with reference to FIG. 4.

At step 410, the method begins.

At step 420, the pixels of the first image are assigned an initial bidirectional reflectance parameter (Bspec) value. As discussed above, Bspec is related to the amount of light striking the sensor in the region of the second image corresponding to the pixel. To continue the example above, an area of glint or glare on the leaf in the image may be assigned a relatively high initial Bspec value (e.g., 0.6), whereas a region that does not reflect as much light (due to incidence angle, leaf damage, or other factors) may be assigned a relatively lower initial Bpsec value (e.g., 0.2). It will be appreciated that these numbers are used for exemplary purposes only, and a different range may be used depending on lighting conditions, leaf type, leaf condition, or the like.

At step 430, the initial Bspec value is used to estimate a first Crab value for some or all of the pixels in the second image. In some embodiments, a triangular green index value for the reflectance image ($TGI_r$) is estimated and is also used to estimate Crab. $TGI_r$ may be calculated in much the same way that $TGI_r$ is estimated in step 140 above, by the relationship:

$$TGI_r = \tfrac{1}{2}(190(R_r - G_r) - 120(R_r - B_r))$$

In some embodiments, reflective model coefficients a, b, c are also determined in order to express the relationship of $TGI_r$ and Bspec to Crab for given values of N and Bspec. In some embodiments, a database of N values and corresponding coefficient values is accessed; coefficients for the value of N selected for use in the current model may be interpolated or otherwise estimated from reflective model coefficients for known values of N. In other embodiments, the coefficient values may be calculated using N and the $R_r$, $G_r$, $B_r$ values.

In one example, a particular strain of corn is known to have an approximate N value of 1.518. Reflective coefficients a, b, c for various values of Bspec for N=1.518 may be accessed. An exemplary table showing exemplary coefficients is shown in Table 2:

TABLE 2

Exemplary reflective coefficients for various values of Bspec where N = 1.518

| Bspec | a | b | c |
|---|---|---|---|
| 0.01 | 0.64482 | −16.978 | 134.58 |
| 0.06 | 0.64482 | −19.684 | 173.05 |

TABLE 2-continued

Exemplary reflective coefficients for various values of Bspec where N = 1.518

| Bspec | a | b | c |
|---|---|---|---|
| 0.11 | 0.64482 | −22.39 | 217.19 |
| 0.16 | 0.64482 | −25.097 | 267.02 |
| 0.21 | 0.64482 | −27.803 | 322.52 |
| 0.26 | 0.64482 | −30.509 | 383.69 |
| 0.31 | 0.64482 | −33.215 | 450.55 |
| 0.36 | 0.64482 | −35.921 | 523.09 |
| 0.41 | 0.64482 | −38.627 | 601.30 |
| 0.46 | 0.64482 | −41.333 | 685.19 |
| 0.51 | 0.64482 | −44.039 | 774.77 |

An estimate of Crab for each pixel may then be determined by a relationship between $TGI_r$ and BSpec for that pixel, and the reflective coefficients:

$$Crab = a(TGI_r^2) + b(BSpec) + c(Bspec)$$

The reflective coefficients for the specific value of N in Table 2 are provided for illustrative purposes only. Reflective coefficients can be calculated for any value of Bspec using the following meta-model for the terms above:

a=0.64482 b(Bspec)=−54.12(Bspec)−16.437 c(Bspec)=1135.7(Bspec$^2$)+689(Bspec)+127

At step 440, a variance of the Crab estimate across the pixels is determined. For example, the variance may be calculated as the squared deviation of Crab of each pixel from the mean Crab estimate for the pixels. Based on the consistent chlorophyll assumption, a determination that Crab estimates for individual pixels varies by a relatively large amount from the mean may indicate that further refinement may be necessary. In some embodiments, the variance of the Crab estimates as well as the mean Crab value may be stored for comparison in later steps.

At step 450, the initial Bspec value for each pixel may be modified according to the Crab estimate determined at step 430. For example, the Bspec value may be reduced for pixels having a relatively high Crab value as determined at step 430. Similarly, the Bspec value may be increased for pixels having a relatively low Crab value as determined at step 430.

At step 460, the process repeats steps 430 and 440 using the modified Bspec values from step 450. In particular, a revised Crab estimate is determined for each pixel using the modified Bspec values, and the variance of these revised Crab estimates is determined. The variance of the revised Crab estimates is compared to the variance of any earlier Crab estimates, with the Crab estimates having a lower variance being preferred.

Steps 430, 440, and 450 may be repeated a number of times, with the Bspec values of the pixels iteratively revised until an acceptably low variance of Crab estimates across the pixels is achieved. In this manner, the method converges on a single Crab estimate. An average, median, mode, or other statistical measure of the low-variance Crab estimates can be performed to determine an estimated Crab value for the leaf. In some embodiments, once variance is minimized in this manner, the estimated Crab value for the leaf is determined only from those pixels having a Bspec estimate within a given sigma variation from the mean. In other words, outlier pixels that have a relatively extreme value of Bspec (e.g., +/−a 1-sigma variation) are excluded from calculating the mean Crab estimate.

Method 400 ends at step 470.

It will be appreciated that the assumption of relatively constant chlorophyll levels across the leaf may be violated by leaf damage or other factors. Therefore, in some embodiments a pre-processing step may be performed at the beginning of method 400 to identify low-variance pixels to be used in converging on a Crab estimate for the leaf. For example, pixels may be clustered (e.g., by a K-means algorithm) according to pixel properties, and only those pixels having properties varying relatively little from the mean of that property for all candidate pixels may be included in later steps.

Returning again to FIG. 1, at step 160, an estimated chlorophyll concentration value for the plant is determined based on the Ctab value estimated at step 140 and the Crab value estimated at step 150. Because the Ctab and Crab estimates are both attempts to measure the chlorophyll a+b level of the leaf, the values should be similar. In some embodiments, the average of the Ctab estimate and the Crab estimate is determined to be the chlorophyll level of the plant. In other embodiments, one of the two values (e.g., Ctab) may be determined to be the chlorophyll level of the plant, with the other value (e.g. Crab) being a check or correction to the other value.

There may be some variation between the Ctab value estimated at step 140 and the Crab value estimated at step 150. Such variation may indicate an inaccurate value of N, leading to selection of improper coefficients in estimating Crab and Ctab. In some embodiments, the value of N can be estimated based on the values of Crab and Crab so that:

$$N=0.0001(Ctab-Crab)^2+0.0124(Ctab-Crab)+1.4878$$

At optional step 170, a refined value of the leaf model parameter N is estimated using this relationship, allowing for recalculation of the values of Ctab and Crab in steps 140 and 150 using coefficients based on the refined value of N. This refinement process may be repeated until the values of Ctab and Crab for a given value of N are nearly identical. The value of N used in the initial run of the process may be a known value of N for a given species of plant, but in reality the index of refraction (and therefore N) for a particular plant may vary from the published value of N.

Method 100 ends at step 180.

Method 100 provides a "spot measurement" of chlorophyll for one or more leafs in a single location (e.g., from a single plant). According to another aspect of the present disclosure, multiple spot measurements can be taken at various locations around a field or region thereof, and the multiple spot measurements may be used to generate a chlorophyll profile (e.g., a map) of the entire field. GPS measurements or other location data may be used to correlate the spot measurements with locations captured in overhead imagery of the field, such as satellite or aerial imagery. Sensor spectral response measurements may be determined from the overhead imagery of the field. Ground-based measurements of the "Leaf Area Index" (the relative area covered by foliage in the field) may be used to refine the spectral response measurements of the overhead imagery.

The spot measurements can be used to correct or calibrate the overhead imagery to generate a full predictive model of the chlorophyll level of the field, which in turn can be used to determine the amount of nitrogen available to the plants at various locations in the field, as well as areas of nitrogen deficiency or surplus. Spot yield measurements and/or historical measurements of yield, chlorophyll level, nitrogen level, or other metrics may be used to further calibrate the full predictive model.

Figure 5:
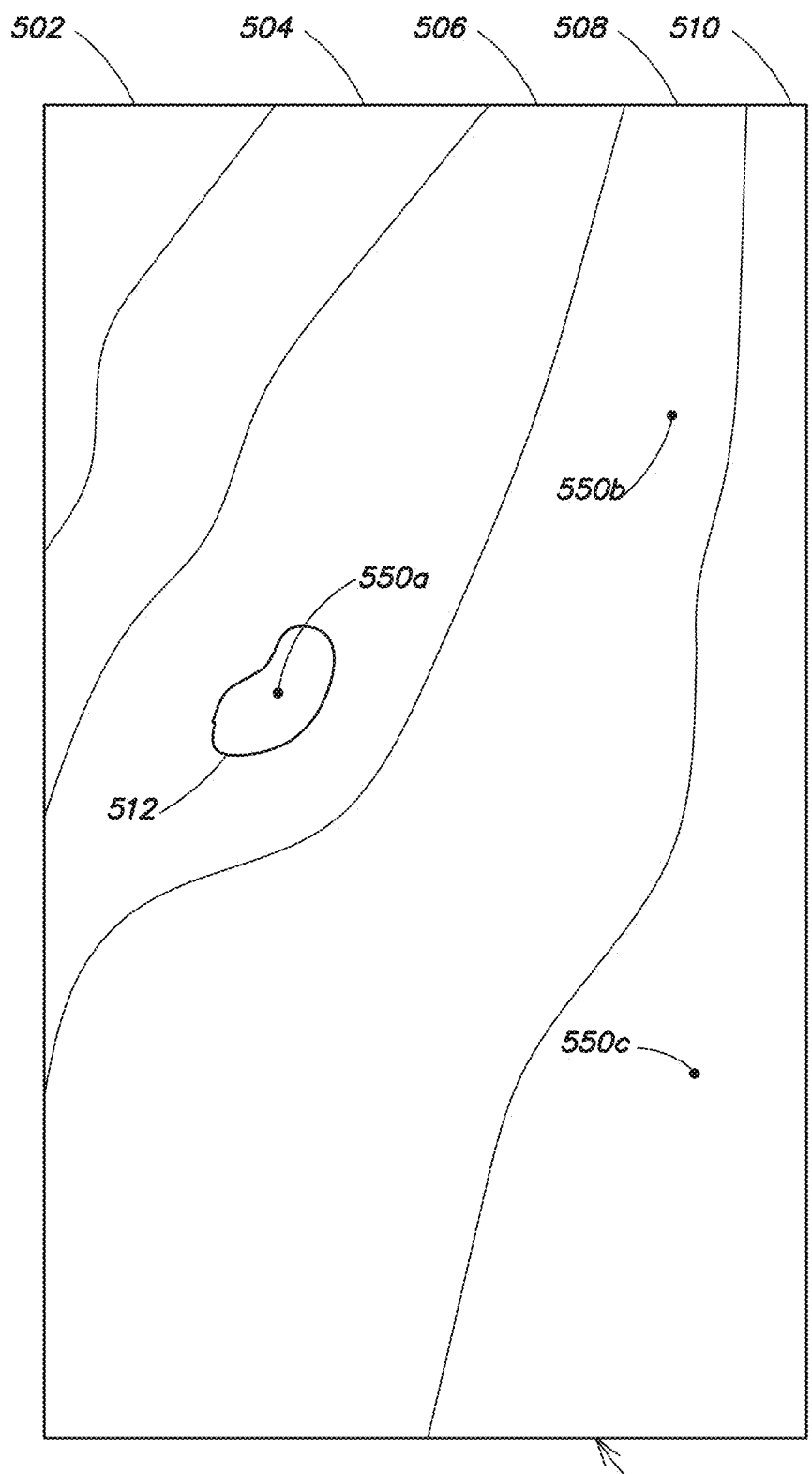
FIG. 5 illustrates an exemplary overhead model of chlorophyll in a field according to aspects of the invention.

FIG. 5 illustrates an exemplary overhead model 500 of chlorophyll in a field according to some embodiments. The overhead model may have been determined using color and/or spectral response measurements of overhead imagery to determine its "greenness," and from that, chlorophyll estimates for portions of the field. The model 500 includes regions 502-512 for which different chlorophyll estimates have been made. The shape, size, and characteristics of regions 502-512 are for illustrative purposes only, and the model 500 may include chlorophyll measurements for regions encompassed by single pixels or pixel blocks of any suitable size.

Locations 550a-c in the field at which spot measurements may be taken are overlaid onto FIG. 5. The spot measurements may be individual chlorophyll estimates performed from images captured at each location as determined in method 100.

Figure 6:
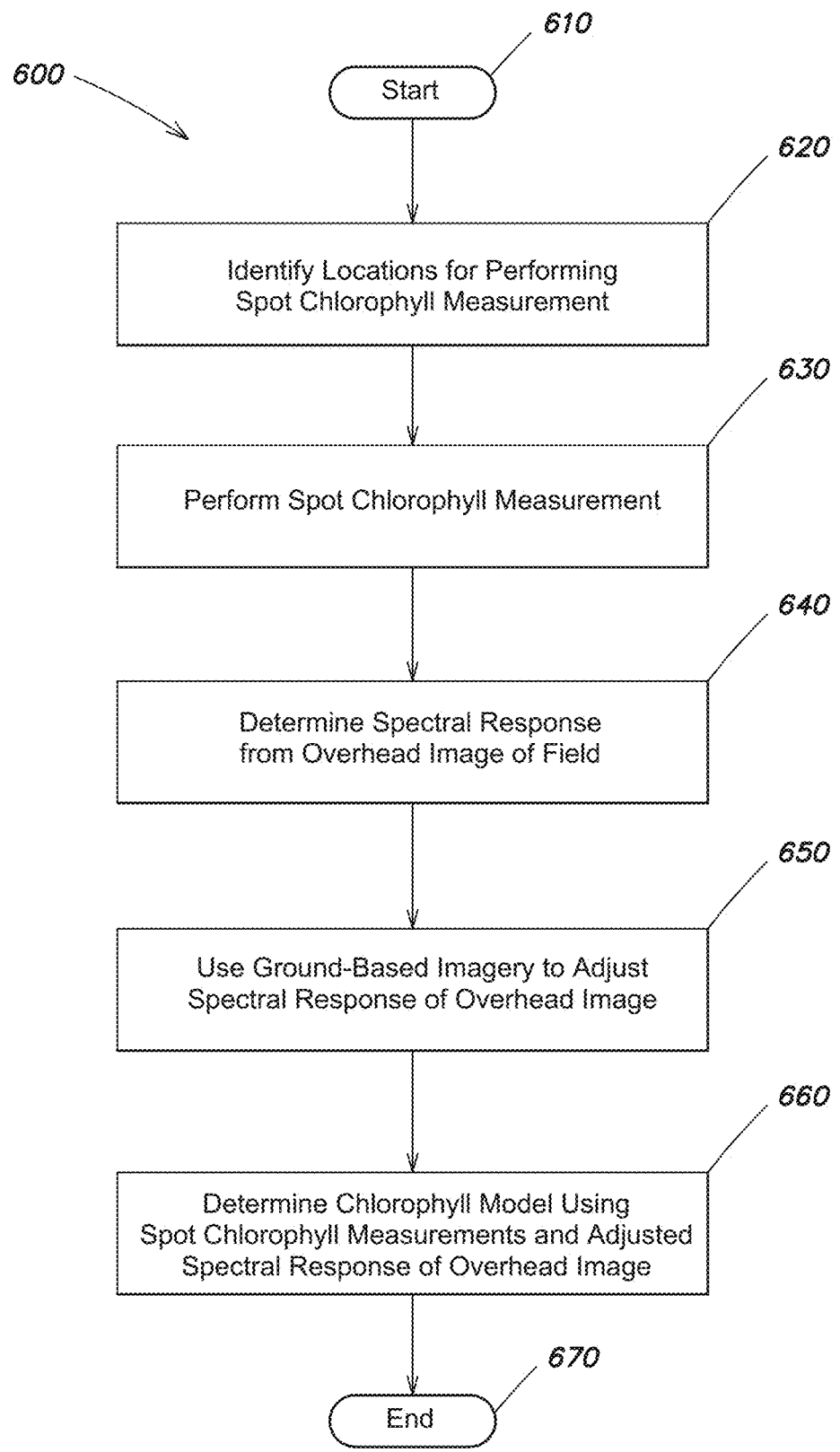
FIG. 6 illustrates an exemplary method of using spot chlorophyll measurements to generate a chlorophyll map of a field as discussed in various embodiments herein.

A method 600 of using spot chlorophyll measurements to generate a chlorophyll map of a field according to one embodiment is discussed with reference to FIG. 6.

At step 610, the method begins.

At optional step 620, one or more locations and/or the number of those locations are selected for performing spot chlorophyll measurements in the field. According to some embodiments, a Monte Carlo technique is performed to estimate the effect on the chlorophyll model of the number of spot measurements, spatial distribution and/or location of the spot measurements, and accuracy of the spot measurements. The Monte Carlo simulation is run based on various combinations of those variables, and the predicted full chlorophyll model is compared to actual information derived from spot measurements or otherwise. The output of the Monte Carlo simulation, and its correlation to actual information for a particular combination of variables, allows for recommendations to be made concerning the number of spot measurements needed, the best spot measurement location configurations, and the required accuracy or tolerance of the spot measurements. According to some embodiments, a map of proposed spot measurements and/or GPS coordinates for taking those measurements is provided. In some embodiments, instructions are provided to guide a person (e.g., using a display or audio component of a mobile device) taking the spot measurements to the proper locations for taking such measurements. In other embodiments, specific locations are not given, but certain constraints are described. For example, it may be recommended that 10 spot measurements be taken, with no spot measurement within 100 meters of another spot measurement.

At step 630, a spot measurement estimate of a chlorophyll concentration value of the first plant in a first region in the field may be determined. The spot measurement may be taken at a location recommended in step 620. As described in step 620, in some embodiments a number of spot measurements may be taken. The spot measurement estimate of a chlorophyll concentration value may be determined from images of light transmitted through and reflected from a leaf according to the steps of method 100. A location, time, weather condition, lighting condition, or other aspect of the spot measurement may be determined (e.g., by using a GPS component) and stored with the spot measurement information.

At step 640, an overhead sensor spectral response of at least one second plant in the first region in the field is detected from an overhead image of the field. According to some embodiments, an overhead TGI value is determined for the portions of the field according to the R, G, B values of pixels in the overhead image. It will be appreciated, however, that an overhead image of the field is likely to contain regions of vegetation (i.e., the crop plant whose chlorophyll is being measured) as well as the bare earth in which the vegetation is growing. Since younger plants are generally smaller than more mature plants, a field with recently-planted crops is likely to contain more pixels representing earth (i.e., dirt) than a field with plants nearly ready for harvest. The different pixel characteristics associated with vegetation and earth lead to a "mixing problem" wherein the reflectance of non-crop material mixes with the chlorophyll signature. The effect of the mixing problem can be minimized by determining the TGI of only the portion of the field covered by vegetation using the Leaf Area Index (LAI).

According to some embodiments, the TGI of the plants in the field is determined using ground based-measurements to correct TGI measurements from overhead imagery. In particular, a ground-based image of at least one plant and surrounding soil is captured, and a ground-based sensor spectral response measurement is determined. A mobile phone user may be instructed to use a mobile device or other digital camera to capture an image from a relatively low angle of one or more rows of crops and the surrounding earth. The image may be captured according to a typical user experience of capturing an image, such as from a height of 3-5 feet above the ground, aiming downward at the ground at a 45 degree angle below horizontal. The user may be instructed to stand between two adjacent rows of crops. A gyroscope or 3-axis accelerometer within the mobile device may be used to determine if the angle of the device is acceptable for capturing the image, or may be used to generate instructions to the user to change the orientation of the mobile device.

According to some embodiments, a portion of a row of crops may be identified in the image using sensor spectral response, color detection, computer vision techniques, or other techniques. According to some embodiments, the pixels of the ground-based image having a sensor spectral response corresponding to what a human would perceive as green vegetation are detected, and the area they occupy in the image may be determined with respect to the remaining pixels.

At step 650, the ground-based image may be used to correct or adjust the TGI values of an overhead image. If the overhead image is of sufficient quality and resolution such that it is possible to identify rows of crops within the overhead image, then the position(s) and area (in pixels) of rows in the ground-based image may also be determined. Areas of vegetation can be detected (e.g., based on the sensor spectral response of the camera), and the portion of the row covered by vegetation can be expressed as $LAI_r$. A TGI value for the plants may be determined using $LAI_r$, wherein the TGI of pixels corresponding to vegetation in individual rows of crops is determined according to the following relationship:

$$TGI_a = \frac{(TGI_{row} - (1 - LAI_r)TGI_{earth})}{LAI_r}$$

$TGI_{row}$ represents the measured TGI on the portion of the image corresponding to the row, and $TGI_{earth}$ represents the measured TGI of the visible earth between the rows as determined from the overhead imagery. $TGI_{earth}$ can be obtained by transforming the ground-based image R, G, B measurements of earth to an estimated response of the overhead sensor pixel when viewing just earth.

In other cases, the overhead image may be of insufficient quality of resolution to resolve individual rows. In that case, a field-based TGI may be determined using $LAI_f$, wherein the TGI of pixels corresponding to vegetation in the field is determined according to the following relationship:

$$TGI_a = \frac{(TGI_{row} - (1 - LAI_r)TGI_{earth})}{LAI_r}$$

$TGI_{field}$ represents the measured TGI of the field generally, and $TGI_{earth}$ represents the measured TGI of the visible earth (i.e., non-vegetation) as determined from the overhead imagery.

Under either model, $TGI_a$ isolates the TGI of the vegetation by reducing the mixing effect of using pixels representing vegetation and earth to calculate TGI. In some embodiments, both a row-based and field-based TGI is determined, with a confidence level determined for the row-based TGI depending on the resolution of the image and other factors. The confidence level is used to determine if the row-based TGI or field-based TGI is to be used for subsequent steps.

At step 660, a full chlorophyll model is determined based on the adjusted overhead TGI values and the spot measurements of chlorophyll values. In particular, a 2D interpolation is performed using the overhead TGI values as dependent variables and using the spot measurement chlorophyll values determined in step 630 (according to method 100) as independent variables. For example, an nth order regression model may be employed. In some embodiments, overhead measures of plant health (such as NDVI or TGI) are positively correlated to ground-based measures of yield, or greenness. Regression models without this constraint may have a good fit to the data, but may give counter-intuitive results for areas in the field having low indicated plant health but high predicted yield or chlorophyll. In some embodiments, such results are avoided by constraining the Nth order model to have N+1 positive correlation coefficients, P(1) . . . P(N+1) such that:

$$Y=P(1)*X^N+P(2)*X^{(N-1)}+ \ldots +P(N)*X+P(N+1)$$

where Y is a vector of M spot measurements (M>N) at M field locations, and X is a vector of overhead measurements (space or aerial) of NDVI, TGI or other plant health indicator at the same M field locations. The spot measurements can be yield estimates from the kernel counter, or chlorophyll estimates.

The N+1 coefficient values are solved using a non-negative least squares algorithm. The algorithm starts with a set of possible basis vectors and computes the associated dual vector lambda. The algorithm then selects the basis vector corresponding to the maximum value in lambda in order to swap out of the basis in exchange for another possible candidate. This continues until lambda is less than or equal to zero. Furthermore, the spot measurements are tested to ensure they cover the full range of expected values. Spot yield measurements may range from a minimum value Ymin to a maximum value Ymax. If the spot measurement vector does not span this range, then Ymin and Ymax are artificially appended. For corn yield, Ymin and Ymax are 50, and 250 bushels/acre, respectively. For chlorophyll, Ymin, and Ymax are 20 and 80 micrograms/cm$^2$, respectively. The X vector may also be expanded when the Y vector is expanded.

For yield, when the overhead plant health measurements are NDVI, Xmin and Xmax are 0.3 and 0.9, respectively. For chlorophyll, when the overhead plant health measurements are TGI, the Xmin and Xmax depends on the average Bspec parameter but is generally between 5 and 25 respectively for average overhead Bspec values less than 0.3. In this manner, overhead TGI values can be used to estimate chlorophyll values in the full chlorophyll model, with the spot measurement chlorophyll values being used to calibrate the model.

The method ends at step 670.

The full chlorophyll model determined in method 600 may be used to generate a nitrogen sufficiency map for the crop, which indicates an estimated amount of nitrogen available to plants in certain regions of the field. In some embodiments, it is recommended to grow a control plot of the crop that has sufficient nitrogen, such as by over-applying nitrogen. The control plot may be designed to represent the crop generally according to one or more aspects, including soil acidity, inherent soil nitrogen content, sunlight, moisture content, and other soil conditions. The control plot may also be part of the larger field for which a full chlorophyll model is generated in method 600. The estimated chlorophyll content of the control plot can then be divided into the chlorophyll estimates of other portions of the field to generate a nitrogen sufficiency profile (e.g., map) providing a nitrogen sufficiency value $N_s$ for other portions of the field. The value $N_s$ may range from 0.0 to 1.0, wherein the nitrogen content of the control plot is defined as 1.0. Regions of the nitrogen sufficiency profile having a value of $N_s$ less than a defined threshold (e.g., 0.9) may be considered for side-dress. In general, the nitrogen application rate may be determined according to the following relationship:

$$N_r = 200(1-N_s)$$

where $N_r$, may be expressed in terms of pounds of nitrogen per acre.

In embodiments where no control plot is available, the interpretation of the chlorophyll results may be determined based at least on the type of crop. For example, it may be determined that for corn, at least 50 micrograms/cm$^2$ of Chlorophyll a+b (Cab) is needed for healthy growth. This target may be used as a normalization factor to product a nitrogen sufficiency map and nitrogen recommendation profile.

In some embodiments, spot measurements of yield estimates of the crop may be used to further calibrate the full chlorophyll model. Yield estimates of grain crop plants (e.g., wheat, corn, rice, or any other grain crop having a seed head) or other plants having seed pods (e.g., a cotton boll) may be determined using methods for automatically estimating a number of seed heads (e.g., corn kernels) using a digital camera of a mobile device. Apparatus and processes for performing such methods are described in U.S. application Ser. No. 15/011,004, filed on Jan. 29, 2016 and titled "APPARATUS AND PROCESSES FOR CLASSIFYING AND COUNTING CORN KERNELS", the contents of which are hereby incorporated in their entirety for all purposes.

The spot yield measurements can be 2D interpolated to give a field map of predicted yield. In particular, a regression may be performed with the overhead TGI values as dependent variables and using spot yield measurements as independent variables. For example, a first- or second-order regression model may be employed. It will be appreciated that any measure of plant health index other than TGI may also be used. For example, the Normalized Vegetation Difference Index (NDVI) may be used as an index of plant health, and may be expressed as:

$$NDVI = \frac{NIR - R}{NIR + R}$$

where R and NIR represent the spectral reflectance measurements acquired in the red and near-infrared regions, respectively.

In some embodiments, historical data for the field and/or crop may also be determined. For example, profiles or maps of previous measurements of yield, chlorophyll, nitrogen sufficiency, or nitrogen application may be employed to modify any nitrogen recommendations determined from the chlorophyll model. In some embodiments, the full yield model and/or the historical data may be used to calibrate the nitrogen application rate. For example, if the chlorophyll model leads suggests that a particular amount of nitrogen be applied, but historical data from a previous year indicates that the yield that year was sufficient using a lower amount of nitrogen, the nitrogen amount suggested may be reduced for the current year. Similarly, if the full yield model for the current year suggests that the yield is estimated to be less than sufficient, the nitrogen amount suggested may be increased for the current year.

According to some embodiments, the historical data may be assigned a relevance score or other measure of its applicability to the current year. For example, historical data from a year with a large amount of precipitation may be given a relatively low relevance score if the current year is experience drought conditions. Similarly, the presence of unforeseen factors in the historical data, such as hail, pest damage, wind, flooding, or the like may also reduce the relevance score of that year where the present year does not include such factors.

Figure 7:
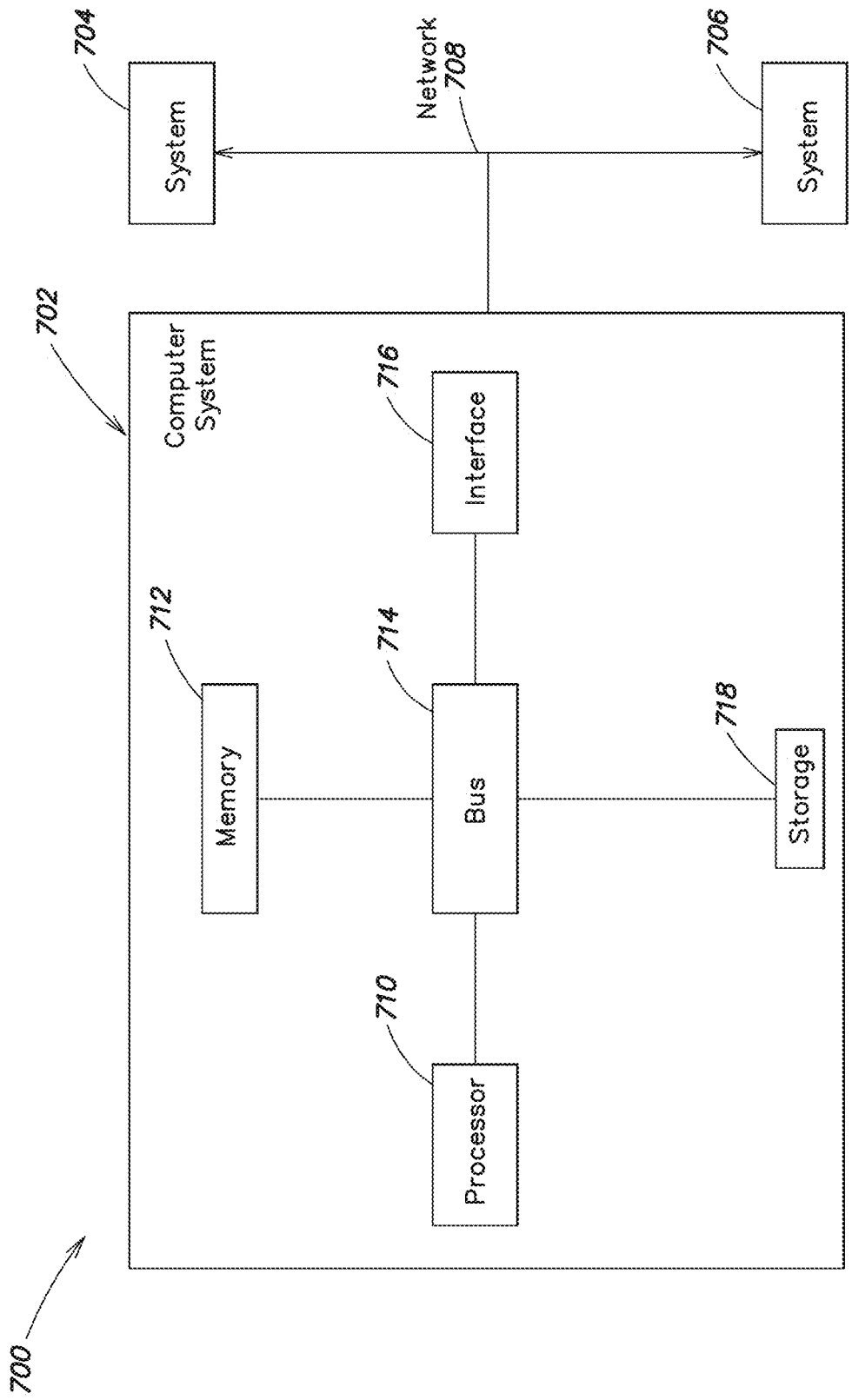
FIG. 7 is a block diagram of one example of a computer system on which aspects and embodiments of the present invention may be implemented.

FIG. 7 is a block diagram of a distributed computer system 700, in which various aspects and functions discussed above may be practiced. The distributed computer system 700 may include one or more computer systems. For example, as illustrated, the distributed computer system 700 includes three computer systems 702, 704 and 706. As shown, the computer systems 702, 704 and 706 are interconnected by, and may exchange data through, a communication network 708. The network 708 may include any communication network through which computer systems may exchange data. To exchange data via the network 708, the computer systems 702, 704, and 706 and the network 708 may use various methods, protocols and standards including, among others, token ring, Ethernet, Wireless Ethernet, Bluetooth, radio signaling, infra-red signaling, TCP/IP, UDP, HTTP, FTP, SNMP, SMS, MMS, SS7, JSON, XML, REST, SOAP, CORBA IIOP, RMI, DCOM and Web Services.

According to some embodiments, the functions and operations discussed for producing a three-dimensional synthetic viewpoint can be executed on computer systems 702, 704 and 706 individually and/or in combination. For example, the computer systems 702, 704, and 706 support, for example, participation in a collaborative network. In one alternative, a single computer system (e.g., 702) can generate the three-dimensional synthetic viewpoint. The computer systems 702, 704 and 706 may include personal computing devices such as cellular telephones, smart phones, tablets, "fablets," etc., and may also include desktop computers, laptop computers, etc.

Various aspects and functions in accord with embodiments discussed herein may be implemented as specialized hardware or software executing in one or more computer systems including the computer system 702 shown in FIG. 7. In one embodiment, computer system 702 is a personal computing device specially configured to execute the processes and/or operations discussed above. As depicted, the computer system 702 includes at least one processor 710 (e.g., a single core or a multi-core processor), a memory 712, a bus 714, input/output interfaces (e.g., 716) and storage 718. The processor 710, which may include one or more microprocessors or other types of controllers, can perform a series of instructions that manipulate data. As shown, the processor 710 is connected to other system components, including a memory 712, by an interconnection element (e.g., the bus 714).

The memory 712 and/or storage 718 may be used for storing programs and data during operation of the computer system 702. For example, the memory 712 may be a relatively high performance, volatile, random access memory such as a dynamic random access memory (DRAM) or static memory (SRAM). In addition, the memory 712 may include any device for storing data, such as a disk drive or other non-volatile storage device, such as flash memory, solid state, or phase-change memory (PCM). In further embodiments, the functions and operations discussed with respect to generating and/or rendering synthetic three-dimensional views can be embodied in an application that is executed on the computer system 702 from the memory 712 and/or the storage 718. For example, the application can be made available through an "app store" for download and/or purchase. Once installed or made available for execution, computer system 702 can be specially configured to execute the functions associated with producing synthetic three-dimensional views.

Computer system 702 also includes one or more interfaces 716 such as input devices (e.g., camera for capturing images), output devices and combination input/output devices. The interfaces 716 may receive input, provide output, or both. The storage 718 may include a computer-readable and computer-writeable nonvolatile storage medium in which instructions are stored that define a program to be executed by the processor. The storage system 718 also may include information that is recorded, on or in, the medium, and this information may be processed by the application. A medium that can be used with various embodiments may include, for example, optical disk, magnetic disk or flash memory, SSD, among others. Further, aspects and embodiments are not to a particular memory system or storage system.

In some embodiments, the computer system 702 may include an operating system that manages at least a portion of the hardware components (e.g., input/output devices, touch screens, cameras, etc.) included in computer system 702. One or more processors or controllers, such as processor 710, may execute an operating system which may be, among others, a Windows-based operating system (e.g., Windows NT, ME, XP, Vista, 7, 8, or RT) available from the Microsoft Corporation, an operating system available from Apple Computer (e.g., MAC OS, including System X), one of many Linux-based operating system distributions (for example, the Enterprise Linux operating system available from Red Hat Inc.), a Solaris operating system available from Sun Microsystems, or a UNIX operating systems available from various sources. Many other operating systems may be used, including operating systems designed for personal computing devices (e.g., iOS, Android, etc.) and embodiments are not limited to any particular operating system.

The processor and operating system together define a computing platform on which applications (e.g., "apps" available from an "app store") may be executed. Additionally, various functions for generating and manipulating images may be implemented in a non-programmed environment (for example, documents created in HTML, XML or other format that, when viewed in a window of a browser program, render aspects of a graphical-user interface or perform other functions). Further, various embodiments in accord with aspects of the present invention may be implemented as programmed or non-programmed components, or any combination thereof. Various embodiments may be implemented in part as MATLAB functions, scripts, and/or batch jobs. Thus, the invention is not limited to a specific programming language and any suitable programming language could also be used.

Although the computer system 702 is shown by way of example as one type of computer system upon which various functions for producing three-dimensional synthetic views may be practiced, aspects and embodiments are not limited to being implemented on the computer system, shown in FIG. 7. Various aspects and functions may be practiced on one or more computers or similar devices having different architectures or components than that shown in FIG. 7.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A method for determining chlorophyll content of a plant, comprising:

capturing a first image comprising light transmitted through a leaf of a plant;

capturing a second image comprising light reflected from the leaf of the plant;

estimating, from a plurality of pixels in the first image, a transmissive chlorophyll concentration value of the leaf;

determining, based on a plurality of pixels in the second image, bidirectional reflectance parameters for the second image;

determining, for the plurality of pixels in the second image, a plurality of reflectance chlorophyll concentration values, each reflectance chlorophyll concentration value being determined based on a respective one of the bidirectional reflectance parameters;

adjusting, based on a variance between the plurality of reflectance chlorophyll concentration values, at least one of the bidirectional reflectance parameters to reduce the variance between the plurality of reflectance chlorophyll concentration values across the plurality of pixels in the second image;

estimating, based on the adjusted bidirectional reflectance parameters, the reflectance chlorophyll concentration value for the leaf; and determining an estimated chlorophyll concentration value for the plant based at least on the transmissive chlorophyll concentration value and the reflectance chlorophyll concentration value.

2. The method of claim 1, wherein the transmissive chlorophyll concentration value and the reflectance chlorophyll concentration value are determined using a leaf model parameter, further comprising:
estimating, from the transmissive chlorophyll concentration value and the reflectance chlorophyll concentration value, a revised leaf model parameter; and
determining a second transmissive chlorophyll concentration value and a second reflectance chlorophyll concentration value using the revised leaf model parameter.

3. The method of claim 2, wherein the revised leaf model parameter is estimated based on a difference between the transmissive chlorophyll concentration value and the reflectance chlorophyll concentration value.

4. The method of claim 1, wherein estimating, from the plurality of pixels in the first image, the transmissive chlorophyll concentration value of the leaf comprises determining, from sensor spectral response characteristics of each pixel in the plurality of pixels in the first image, a triangular greenness index (TGI) for the pixel.

5. The method of claim 1, further comprising:
capturing a third image comprising light passed through a first optical reference and a fourth image comprising light passed through a second optical reference, the first optical reference and second optical reference having transmissive characteristics corresponding to known transmissive chlorophyll levels; and
adjusting the transmissive chlorophyll concentration value of the leaf with reference to the known transmissive chlorophyll levels.

6. The method of claim 5, wherein the first optical reference has transmissive characteristics corresponding to a known low transmissive chlorophyll level, and wherein the second optical reference has transmissive characteristics corresponding to a known high transmissive chlorophyll level.

7. The method of claim 1, further comprising:
estimating, using a bidirectional reflectance parameter for each pixel in the plurality of pixels, a first reflectance chlorophyll concentration pixel value for each pixel in the plurality of pixels;
determining a first variance of the first reflectance chlorophyll concentration pixel value across the plurality of pixels;
modifying the bidirectional reflectance parameter for at least one pixel in the plurality of pixels;
estimating, using the modified bidirectional reflectance parameter for the at least one pixel, a second reflectance chlorophyll concentration pixel value for each pixel in the plurality of pixels;
determining a second variance of the second reflectance chlorophyll concentration pixel value across the plurality of pixels;
responsive to the first variance being less than the second variance, estimating the reflectance chlorophyll concentration value based on the first reflectance chlorophyll concentration pixel value of the leaf for each pixel in the plurality of pixels; and
responsive to the second variance being less than the first variance, estimating the reflectance chlorophyll concentration value based on the second reflectance chlorophyll concentration pixel value of the leaf for each pixel in the plurality of pixels.

8. The method of claim 7, wherein modifying the bidirectional reflectance parameter for at least one pixel in the plurality of pixels comprises:
responsive to the at least one pixel in the plurality of pixels having a relatively high first reflectance chlorophyll concentration pixel value, adjusting the bidirectional reflectance parameter of the at least one pixel to be lower; and
responsive to the at least one pixel in the plurality of pixels having a relatively low first reflectance chlorophyll concentration pixel value, adjusting the bidirectional reflectance parameter of the at least one pixel to be higher.

9. The method of claim 7, wherein estimating the reflectance chlorophyll concentration value based on the second reflectance chlorophyll concentration pixel value of the leaf for each pixel in the plurality of pixels comprises determining a mean of the second reflectance chlorophyll concentration pixel value of the leaf for the plurality of pixels.

10. The method of claim 9, further comprising excluding, from the determination of the mean, pixels having a modified bidirectional reflectance parameter not within a defined deviation amount.

11. The method of claim 7, wherein the bidirectional reflectance parameter is an initial bidirectional reflectance parameter, further comprising setting an initial bidirectional reflectance parameter for at least one pixel in the plurality of pixels, the initial bidirectional reflectance parameter determined by the sensor spectral response measurement of the at least one pixel.

12. The method of claim 11, further comprising setting a first initial bidirectional reflectance parameter of 0.6 for at least one pixel having a highest sensor spectral response measurement in the plurality of pixels, and setting a second initial bidirectional reflectance parameter of 0.0 for at least one pixel having a lowest sensor spectral response measurement in the plurality of pixels.

13. The method of claim 1, wherein the plant is a first plant further comprising:
estimating a second transmissive chlorophyll concentration value and a second reflectance chlorophyll concentration value for at least a second plant in a crop field including the first plant; and
generating a model of plant health for the crop field based at least on the transmissive chlorophyll concentration value, the reflectance chlorophyll concentration value, the second transmissive chlorophyll concentration value and the second reflectance chlorophyll concentration value.

14. The method of claim 13, wherein the model of plant health for the crop field is a chlorophyll model indicating an estimated chlorophyll level of plants in a plurality of locations in the crop field.

15. The method of claim 1, wherein the plant is a corn plant.

16. An image processing system comprising:
a memory;
an image receiving component; and
a processor configured to:
capture a first image comprising light transmitted through a leaf of a plant;
capture a second image comprising light reflected from the leaf of the plant;

estimate, from a plurality of pixels in the first image, a transmissive chlorophyll concentration value of the leaf;

determine, based on a plurality of pixels in the second image, bidirectional reflectance parameters for the second image;

determine, for the plurality of pixels in the second image, a plurality of reflectance chlorophyll concentration values, each reflectance chlorophyll concentration value being determined based on a respective one of the bidirectional reflectance parameters;

adjust, based on a variance between the plurality of reflectance chlorophyll concentration values, at least one of the bidirectional reflectance parameters to reduce the variance between the plurality of reflectance chlorophyll concentration values across the plurality of pixels in the second image;

estimate, based on the adjusted bidirectional reflectance parameters, the reflectance chlorophyll concentration value for the leaf; and determine an estimated chlorophyll concentration value for the plant based at least on the transmissive chlorophyll concentration value and the reflectance chlorophyll concentration value.

17. The image processing system of claim 16, wherein the image receiving component is a digital camera of a mobile device.

18. The image processing system of claim 16, further comprising a first optical reference and a second optical reference, the first optical reference and second optical reference having transmissive characteristics corresponding to known transmissive chlorophyll levels, wherein the processor is further configured to:

capture a third image comprising light passed through the first optical reference and a fourth image comprising light passed through the second optical reference; and adjust the transmissive chlorophyll concentration value of the leaf with reference to the known transmissive chlorophyll levels.

19. The image processing system of claim 16, wherein the processor is further configured to:

estimate, using a bidirectional reflectance parameter for each pixel in the plurality of pixels, a first reflectance chlorophyll concentration pixel value for each pixel in the plurality of pixels;

determine a first variance of the first reflectance chlorophyll concentration pixel value across the plurality of pixels;

modify the bidirectional reflectance parameter for at least one pixel in the plurality of pixels;

estimate, using the modified bidirectional reflectance parameter for the at least one pixel, a second reflectance chlorophyll concentration pixel value for each pixel in the plurality of pixels;

determine a second variance of the second reflectance chlorophyll concentration pixel value across the plurality of pixels;

responsive to the first variance being less than the second variance, estimate the reflectance chlorophyll concentration value based on the first reflectance chlorophyll concentration pixel value of the leaf for each pixel in the plurality of pixels; and responsive to the second variance being less than the first variance, estimate the reflectance chlorophyll concentration value based on the second reflectance chlorophyll concentration pixel value of the leaf for each pixel in the plurality of pixels.

20. The image processing system of claim 19, wherein the processor is further configured to modify the bidirectional reflectance parameter for at least one pixel in the plurality of pixels by:

responsive to the at least one pixel in the plurality of pixels having a relatively high first reflectance chlorophyll concentration pixel value, adjusting the bidirectional reflectance parameter of the at least one pixel to be lower; and responsive to the at least one pixel in the plurality of pixels having a relatively low first reflectance chlorophyll concentration pixel value, adjusting the bidirectional reflectance parameter of the at least one pixel to be higher.

* * * * *